(12) United States Patent
Bloess

(10) Patent No.: US 7,005,640 B2
(45) Date of Patent: Feb. 28, 2006

(54) METHOD AND APPARATUS FOR THE CHARACTERIZATION OF A DEPTH STRUCTURE IN A SUBSTRATE

(75) Inventor: Harald Bloess, Radebeul (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 11/008,643

(22) Filed: Dec. 10, 2004

(65) Prior Publication Data

US 2005/0139768 A1 Jun. 30, 2005

(30) Foreign Application Priority Data

Dec. 11, 2003 (DE) ................. 103 58 036

(51) Int. Cl.
| | |
|---|---|
| H01L 21/8234 | (2006.01) |
| G01N 23/00 | (2006.01) |
| G21K 7/00 | (2006.01) |
| A61N 5/00 | (2006.01) |
| G21G 5/00 | (2006.01) |

(52) U.S. Cl. .............. 250/309; 250/306; 250/307; 250/310; 250/492.1; 250/492.3
(58) Field of Classification Search ............ None
See application file for complete search history.

(56) References Cited

U.S. PATENT DOCUMENTS

| | | | | |
|---|---|---|---|---|
| 5,453,617 | A | * | 9/1995 | Tsuneta et al. ............ 250/311 |
| 5,650,621 | A | * | 7/1997 | Tsuneta et al. ............ 250/311 |
| 6,268,608 | B1 | | 7/2001 | Chandler |
| 2003/0098416 | A1 | | 5/2003 | Shemesh et al. |
| 2005/0139768 | A1 | * | 6/2005 | Bloess ..................... 250/309 |

FOREIGN PATENT DOCUMENTS

| | | |
|---|---|---|
| EP | 1209737 | 5/2002 |
| JP | 8298275 A | 11/1996 |

OTHER PUBLICATIONS

Jeremy D. Russell et al. (2003) "A Method for Exact Determination of DRAM Deep Trench Surface Area," Proceedings from the 29th International Symposium for Testing and Failure Analysis, Nov. 2003, pp. 140-143.
German Examination Report dated Aug. 25, 2004.

* cited by examiner

Primary Examiner—John R. Lee
Assistant Examiner—Bernard E. Souw
(74) Attorney, Agent, or Firm—Morrison & Foerster LLP

(57) ABSTRACT

The present invention provides a method for the characterization of a depth structure in a substrate at a surface of the substrate, in which a cutout is produced at the surface of the substrate between an imaging device and the depth structure, the cutout being spaced apart from the depth structure. A layer of the substrate, which incipiently cuts the depth structure and the cutout, is removed by means of an ion beam in order to obtain a cut area, the layer and the normal to the area of the surface of the substrate assuming an acute angle that is greater than zero. The cut area is imaged by means of the imaging device in order to characterize the depth structure.

9 Claims, 5 Drawing Sheets

METHOD AND APPARATUS FOR THE CHARACTERIZATION OF A DEPTH STRUCTURE IN A SUBSTRATE

CLAIM FOR PRIORITY

This application claims priority to Application No. 103 58 036.0, which was filed in the German language on Dec. 11, 2003.

TECHNICAL FIELD OF THE INVENTION

The present invention relates to a method and an apparatus for the characterization of a depth structure in a substrate at a surface of the substrate.

BACKGROUND OF THE INVENTION

In semiconductor fabrication, in particular, structures having a large ratio between the depth measured perpendicular to the surface of a substrate and the lateral dimensions (HAR structures, HAR=high aspect ratio) are increasingly being produced and used, for example for capacitors in memory cells of memory components. Structures of this type have to be characterized at least on the basis of random sampling in the course of production, their dimensions, in particular, being determined in order to monitor the production line and, if appropriate, to track process parameters. This characterization is conventionally done for example by breaking the semiconductor substrate, a structure arranged at the edge of the break subsequently being imaged by scanning electron microscopy, scanning force microscopy or in some other suitable way in order to characterize it and, in particular, to determine its dimensions from the imaging. Principally in the case of laterally small structures, the substrate must contain a multiplicity thereof in order that at least one is situated at the edge of the break. The breaking of the wafer generally precludes further processing thereof.

In an alternative method, a cutout serving as a viewing window is produced in the substrate by means of a focused ion beam, which cutout incipiently cuts the depth structure. The cutout is arranged and formed in such a way that the incipiently cut structure can subsequently be detected or imaged by scanning electron microscopy by means of an electron beam that is obliquely incident on the incipiently cut structure.

What is problematic about this method is the so-called "waterfall effect", which stems from the unavoidable expansion of the focused ion beam and results in the incipiently cut structure being altered while it is actually being incipiently cut. The waterfall effect can be minimized or avoided in the case of a simple structure by prior deposition of a protection cap. For HAR structures, however, there is no conventional method for avoiding the waterfall effect.

SUMMARY OF THE INVENTION

The present invention relates to a method and an apparatus for the characterization of a depth structure in a substrate at a surface of the substrate, the depth structure being, in particular, a cutout or a cutout having a large ratio between depth and lateral dimension or else a structure made of a material that differs from the material of the substrate, thereof the corrupting influence of the waterfall effect is avoided or reduced.

One embodiment of the present invention provides a method for the characterization of a depth structure in a substrate at a surface of the substrate, including:

a) production of a cutout at the surface of the substrate between an imaging device and the depth structure, the cutout being spaced apart from the depth structure;

b) removal of a layer of the substrate, which incipiently cuts the depth structure and the cutout, by means of an ion beam in order to obtain a cut area, the layer and the normal to the area of the surface of the substrate assuming an acute angle that is greater than zero; and c) imaging of the cut area by means of the imaging device in order to characterize the depth structure.

Another embodiment of the present invention provides an apparatus for the characterization of a depth structure in a substrate at a surface of the substrate, having a device for removing a layer of the substrate, which incipiently cuts the depth structure and a cutout at the surface of the substrate by means of an ion beam in order to obtain a cut area; and a device for imaging the cut area through the cutout in order to characterize the depth structure, wherein the removal device is formed in such a way that the layer and the normal to the area of the surface of the substrate assume an acute angle that is greater than zero.

The present invention is based on no longer incipiently cutting the depth structures in a plane perpendicular to the surface of the substrate and thus parallel to the main extent of the depth structure, but rather obliquely. In contrast to the conventional perpendicular cut area, the oblique cut area includes a significantly smaller cross-sectional area of the depth structure. In particular, the cross-sectional area in the case of an HAR structure is significantly shorter in the case of an oblique cut area than in the case of a vertical cut area. This is advantageous since the altering action of the waterfall effect on the cross-sectional area greatly depends on the length of the cross-sectional area as measured in the direction of the focused ion beam. In particular, an action of the waterfall effect that widens the cross-sectional area increases in the direction of movement of the ions. A short cross-sectional area in the direction of the ion beam in the oblique cut area is therefore slightly altered primarily in its width.

In the case of the oblique incipient cut of the depth structure according to the invention, the waterfall effect even has a positive effect if a width of the cross-sectional area that is measured perpendicular to the direction of the ion beam and parallel to the surface of the substrate is detected for the characterization of the depth structure. The waterfall effect lengthens the depth structure and thus the cross-sectional area in the direction of the ion beam. The width of the cross-sectional area therefore changes more slowly in the direction parallel to the ion beam than would be the case without the waterfall effect. To put it another way, the maximum of the width of the cross-sectional area is widened, the maximum width being altered insignificantly. Consequently, the location at which the width of the cross-sectional area is detected is less critical. This is advantageous primarily in the case of an automatic evaluation of the imaging of the cut area with the cross-sectional area or an automatic detection of the width of the cross-sectional area from the imaging.

If the depth structure is intended to be characterized on the basis of its width in a manner dependent on the depth, steps a), b) and c) are executed multiply in order to characterize the depth structure on the basis of imagings of cut areas in a plurality of depths.

In one embodiment of the invention, an apparatus is preferably distinguished by the fact that the removal device and the imaging device are arranged at a vacuum vessel in such a way that the removal and the imaging can be effected without moving the substrate, or, in particular, having to transport it from one vacuum vessel to another vacuum vessel.

BRIEF DESCRIPTION OF THE DRAWINGS

Preferred exemplary embodiments of the present invention are explained in more detail below with reference to the accompanying figures, in which.

DETAILED DESCRIPTION OF THE INVENTION

Figure 1A:
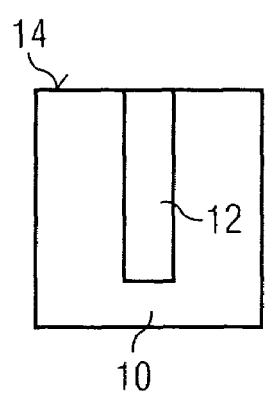
FIG. 1 shows schematic sectional illustrations for describing a conventional method.
Figure 1B:
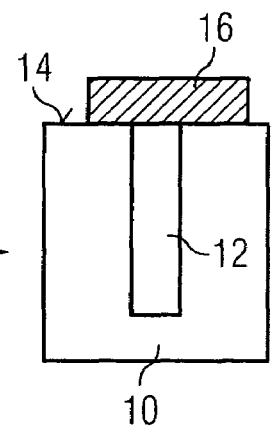
Figure 1C:
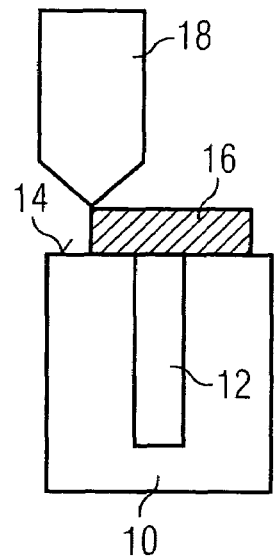
Figure 1D:
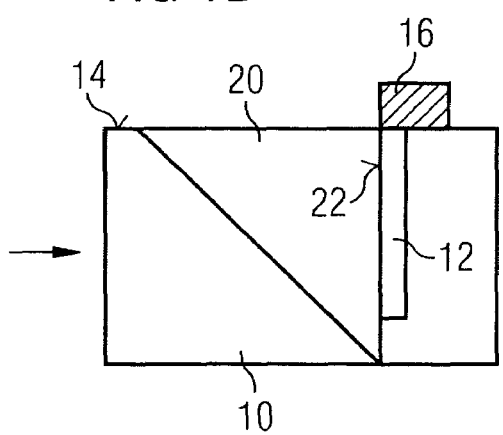
Figure 1E:
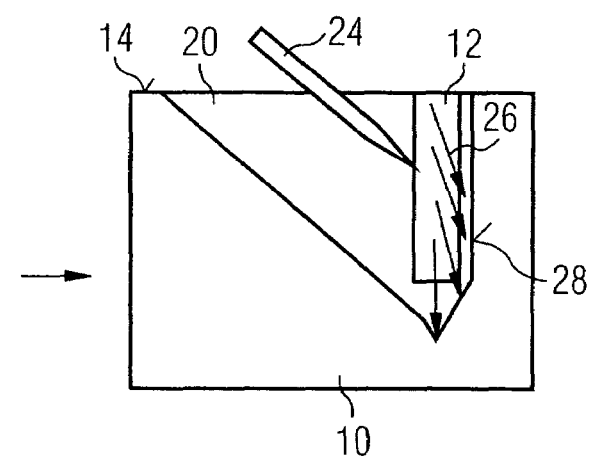

FIG. 1 shows schematic sectional illustrations A, B, C, D, E of a substrate 10 in different stages of a conventional method for the characterization of a depth structure 12 in the substrate 10 at a surface 14 of the substrate 10. The depth structure 12 is in this case an HAR structure. After the production of the depth structure 12, the latter is covered by a protection cap 16 (subfigure B). Afterward, a cutout 20 is produced by means of a focused ion beam 18 (preferably Ga ions; subfigure C), the cutout having a triangular cross section in the vertical section illustrated (subfigure D). The focused ion beam 18 in this case runs parallel to the depth structure 12 or the main extent thereof, i.e. perpendicular to the surface 14 of the substrate 10. A cut area 22 arises with the cutout 20, the cut area being arranged parallel to the focused ion beam 18 and thus perpendicular to the surface 14 of the substrate 10 and parallel to the depth structure 12. The cutout 20 incipiently cuts the depth structure, so that the cut area 22, which for the rest is planar, has a depression that stems from the depth structure 12 or whose cross-sectional area is a vertical cross-sectional area of the depth structure 12. The cutout 20 serves as a viewing window in order subsequently to scan or image the cut area 22 by means of a scanning electron microscope or the focused electron beam 24 thereof at an oblique angle (subfigure E).

The focused ion beam 18 is actually not ideally linear, but rather slightly expanded for various reasons. As is indicated in subfigure E by the arrows 26, material of the substrate outside the ideal shape of the cutout 20 is therefore also removed during the production of the cutout 20. This has the effect, in particular, of altering the geometry of the depth structure 12 (indicated by the surface 28) as soon as it is incipiently cut by the cutout 20. The image of the depth structure 12 incipiently cut by the cut area 22, which image is subsequently detected by means of the electron beam 24, therefore does not show the depth structure in its original geometry, but rather, in particular, with an enlarged width and an enlarged depth (measured perpendicular to the surface 14).

Figure 2:
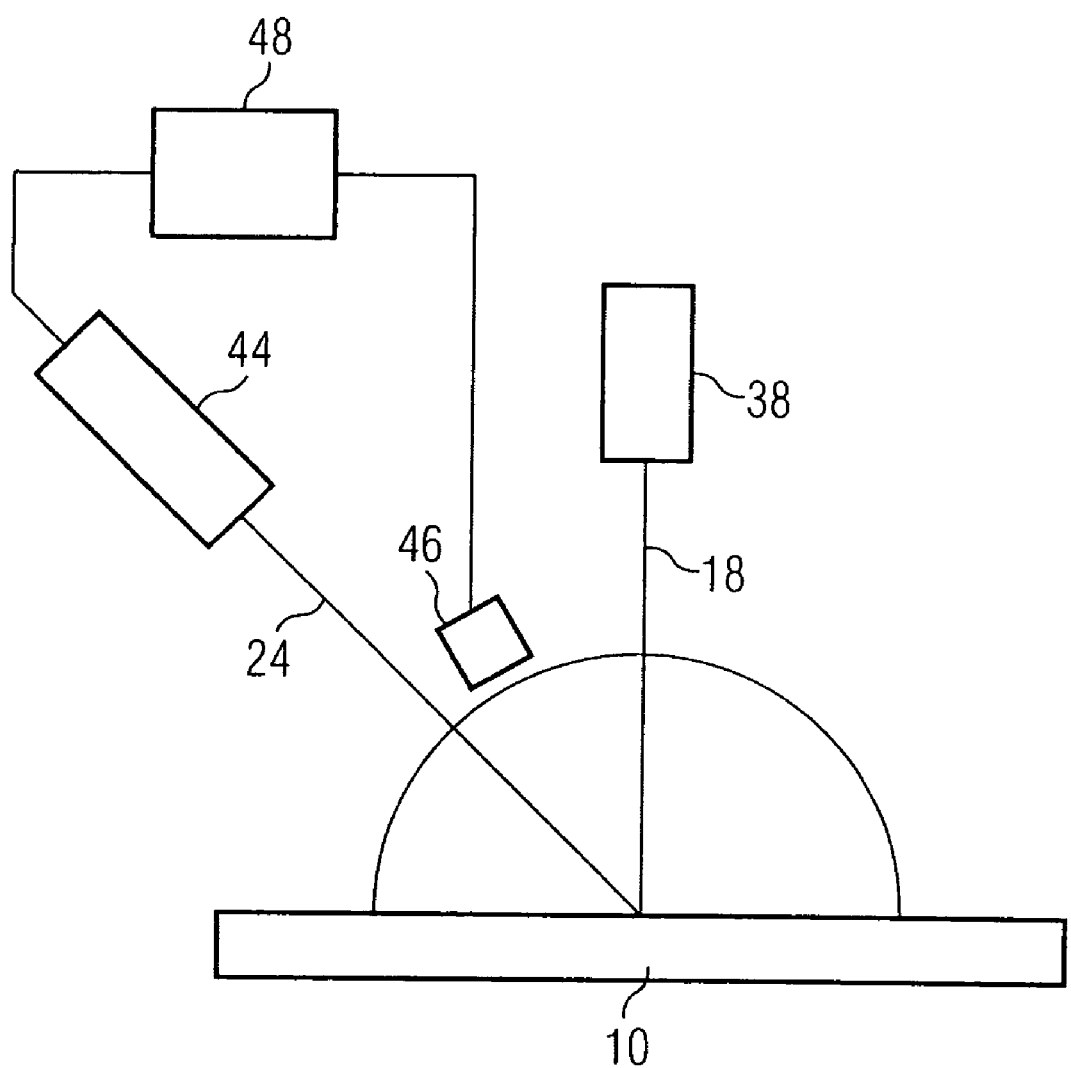
FIG. 2 shows a schematic illustration of a conventional apparatus.
Figure 3A:
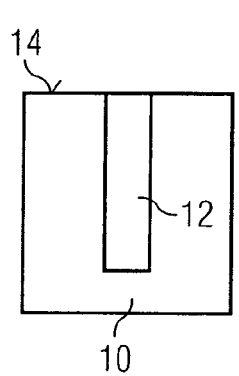
FIG. 3 shows schematic sectional illustrations for describing a method according to the present invention.
Figure 3B:
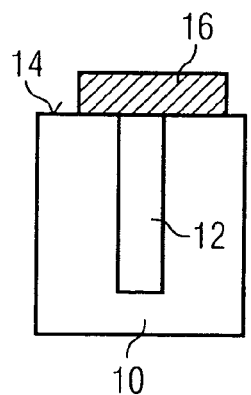
Figure 3C:
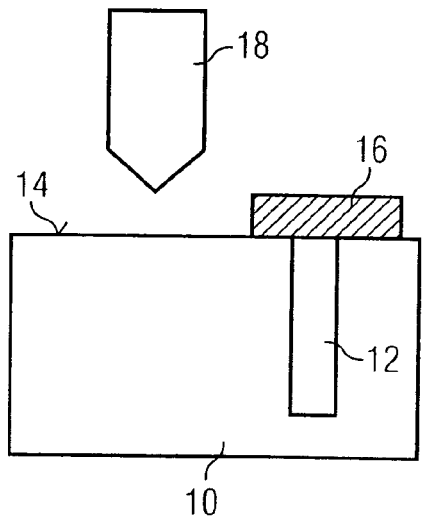
Figure 3D:
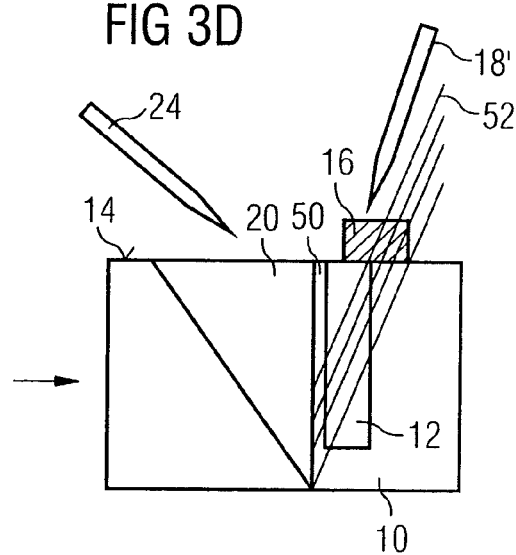

FIG. 2 is a schematic illustration of a conventional apparatus for carrying out the conventional method illustrated above with reference to FIG. 1 at the substrate 10. The apparatus comprises a device 38 for generating the focused ion beam 18 and a device 44 for generating the electron beam 24. The interaction products (secondary electrons, X-rays, etc.) generated by the electrons of the electron beam 24 at the substrate 10 and, in particular, at the cut area 22 (FIG. 1) are detected by a detector 46. The device 44 for generating the electron beam 24, the detector 46 and a control and evaluation unit 48 together form a scanning electron microscope, the control and evaluation unit 48 generating an image of the scanned surface by detecting the temporal correlation of the interaction products detected by the detector 46 and the instantaneous location onto which the electron beam 26 is directed.

FIG. 3 shows schematic sectional views of a substrate 10 with a depth structure 12 at a surface 14 of the substrate 10 in different stages of a method according to the present invention. The depth structure 12 is an arbitrary structure extending from the surface 14 of the substrate 10 into the depth. To put it another way, the depth structure 12 has a finite extent in the direction perpendicular to the surface 14 of the substrate 10. The present invention is particularly suitable as well for a depth structure having a large ratio between the vertical dimension measured in the direction perpendicular to the surface of the substrate and the lateral dimension or dimensions measured in the direction parallel to the surface. By way of example, the depth structure 12 at least approximately has the form of a cylinder with a circular, square, rectangular or arbitrary other base area. The depth structure is either a cutout or a cavity or else it has a material that differs from the surrounding material of the substrate 10. The present invention can be advantageously employed particularly in the case of a depth structure which is hollow or unfilled or else has a material or is filled with a material which is removed by the focused ion beam 24 or the ions thereof more rapidly than the surrounding material of the substrate 10.

Preferably, the depth structure 12 is firstly covered by a protection cap 16 made of W, $SiO_2$, Pt or some other suitable material in order to protect it as long as possible against an action of the ions of the focused ion beam 18 (subfigure B). Afterward, the ion beam 18 produces a cutout 20 that extends near to the depth structure but does not incipiently cut the latter. To put it another way, at least one thin wall 50 made of the material of the substrate 10 remains between the cutout 20 and the depth structure 12 with the result that no ions of the focused ion beam 18 can penetrate into the depth structure 12 and alter the latter (subfigure D). The cutout 20 is preferably produced by a focused ion beam 18 which is particularly preferably incident perpendicularly to the surface 14 of the substrate 10. As an alternative, the cutout 20 is produced by some other suitable method, for example by a wet or dry etching method, an anisotropic dry etching method being particularly suitable in order to produce the cutout 20 as closely as possible next to the depth structure 12 and at the same time to ensure that the wall 50 has a uniform thickness but no holes.

Afterward, the depth structure is incipiently cut obliquely by means of a focused ion beam 18'. For this purpose, as illustrated in subfigure D, the ion beam 18' is tilted relative to the cutout 20. To put it another way, the direction of the focused ion beam 18 assumes an acute angle with respect to the normal to the area of the surface 14 of the substrate 10, said angle being greater than zero. In this case, the material that surrounds the depth structure 12 and, if appropriate, also the material that fills said depth structure is removed in layers running obliquely between the surface 14 of the substrate 10 and the cutout 20. The result is one or preferably successively a plurality of cut areas—tilted with respect to the normal to the area of the surface 14 of the substrate 10—parallel to the cut planes 52. After the removal of each individual layer or after the uncovering of each individual cut plane 52, the cut area currently uncovered is scanned by the focused electron beam 24 of a scanning electron microscope in order to image the cut area with the cross-sectional area of the depth structure 12 contained therein along the cut plane 52. In this case, the cutout 20 serves as a viewing window which is arranged between the device for generating the focused electron beam and the depth structure 12 and through which the focused electron beam 24 falls onto the cut plane. The direction of the focused electron beam 24 and the orientation of the cut planes 52 are in this case preferably chosen in such a way that the direction of the focused electron beam 24 and the normal to the area of the cut plane 52 assume an angle that is as small as possible, and preferably in such a way that the normals to the area of the cut plane 52 and of the surface 14 of the substrate 10 and also the direction of the focused electron beam 24 lie in one plane.

Figure 4:
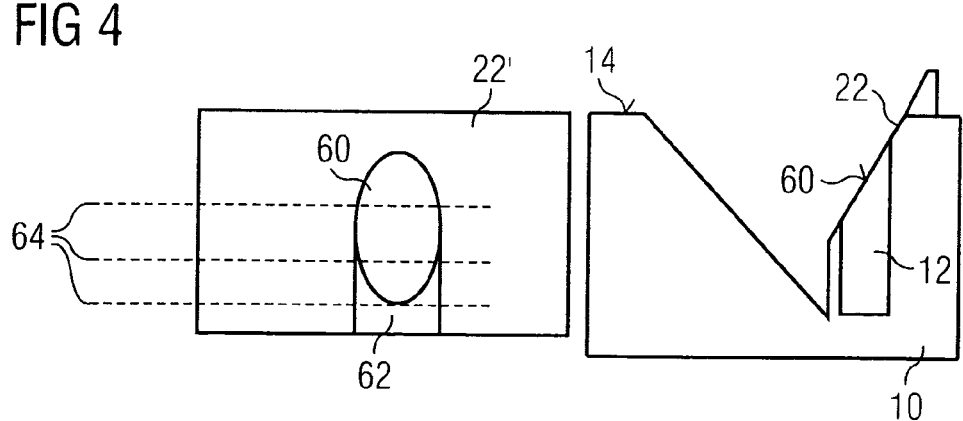
FIG. 4 shows schematic illustrations for describing a method according to the present invention.

In FIG. 4, the situation after uncovering a cut area 22' along one of the cut planes 52 from FIG. 3 is illustrated on the right. The image of the cut area 22' obtained by scanning electron microscopy is illustrated schematically on the left. Since the cut area 22' incipiently cuts the depth structure 12, it has a cross-sectional area 60 thereof. In the present case, the depth structure 12 is cylindrical and has a circular or elliptical base area. The cross-sectional area 60 in the cut area 22' is therefore elliptical.

On account of the waterfall effect already described in the introduction, the focused electron beam 18' also produces an alteration of the cross-sectional area 60 in the course of the cut area 22' being uncovered in accordance with the invention. In particular, the waterfall effect lengthens the cross-sectional area 60 "downstream" in the direction of the focused ion beam. This means, in particular, that the material of the substrate 10 is removed to an intensified extent within a zone 62 lying outside the ideal cross-sectional area 60, so that there the material surface finally lies below the plane of the cut area 22. Therefore, the image of the cut area 22' which is obtained by scanning electron microscopy and is illustrated on the left in FIG. 4 does not show the ideal cross-sectional area 60, but rather a cross-sectional area 60 extended by the zone 62.

This action of the waterfall effect is not disadvantageous, however, but rather in many cases advantageous, as is described below. This advantage is based on the fact that the width of the zone 62 essentially corresponds to the width of the cross-sectional area 60. The width increases slowly "downstream". Consequently, during an automatic detection of the width of the cross-sectional area 60 the location at which the width is measured is not very critical. Irrespective of that location from the locations represented by the dash-dotted lines 64 at which the width is actually measured, the actual width of the cross-sectional area 60 or of the depth structure 12 is in any event detected to a good approximation or with little error.

As already mentioned, preferably a plurality of layers are removed successively by means of the focused ion beam 18' (FIG. 3), thereby successively uncovering a plurality of cut areas 22' in different depths. Each of the cut areas 22' is imaged by electron microscopy in order to obtain images, as illustrated on the left of FIG. 4, which are subsequently measured in order, by way of example, to obtain the width of the depth structure 12 in the different depths.

Figure 5:
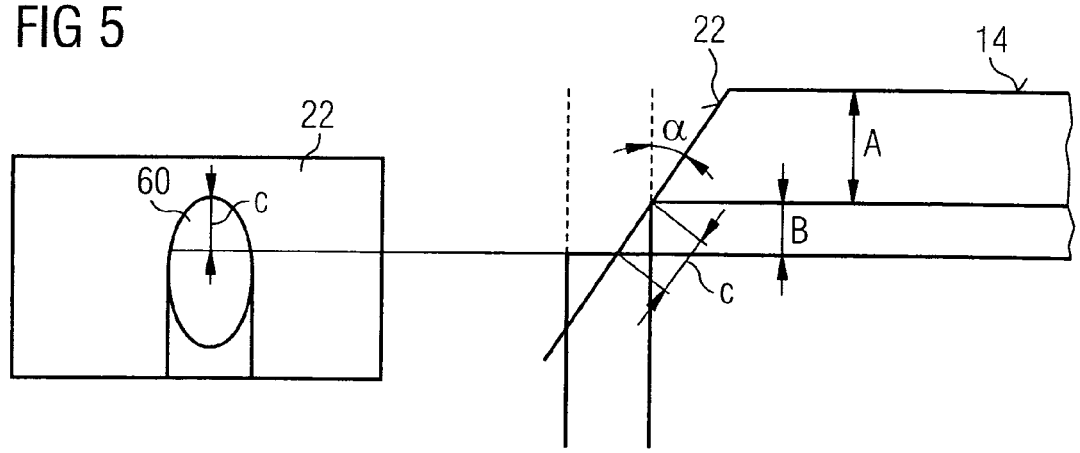
FIG. 5 shows schematic illustrations for describing a method according to the present invention.

As is illustrated below with reference to FIG. 5, a simple trigonometrical relationship exists between the depth T=A+B at which the width of the depth structure 12 is determined and other quantities that are known or can easily be determined. In this case, the depth is the vertical distance from the plane of the surface 14 of the substrate 10. A is the depth of the "front" or upper end of the cross-sectional area 60. C is the distance between said upper end of the cross-sectional area 60 and the location at which the width is determined. C can readily be determined from the image of the cut area 22' illustrated on the left in FIG. 5 and is preferably determined at the same time as the width. B is the projection of C onto the vertical. α is the angle between the cut plane 52 in which the cut area 22' is situated and the normal to the area of the surface 14 of the substrate 10. The following holds true:

$$T = A + B = A + C \cdot \sin(\alpha)$$

The method illustrated with reference to FIGS. 3, 4 and 5 can be used to determine the width of the depth structure 12 in a plurality of depths or as a (discrete) function of the depth. As an alternative, other parameters are obtained from the imagings of the cut areas 22' in order to characterize the depth structure 12. In accordance with a preferred exemplary embodiment, a two-dimensional image of a vertical cut through the depth structure 12 is synthesized from the data obtained. As an alternative, a three-dimensional tomogram of the depth structure is synthesized.

The method described does not require the substrate 10 to be broken. Therefore, it is possible to carry out a larger number of experiments on a single substrate and to obtain a larger number of meaningful and reliable results. If a plurality of depth structures 12 or else more complex structures are processed in a substrate, the influence of different process steps on the structure can be studied on one and the same substrate (10).

For this purpose, the processing is temporarily interrupted in each case after the corresponding process steps in order in each case to characterize one or a plurality of the structures processed thus far, as described above with reference to FIGS. 3, 4 and 5. In this case, the cutout 20 preferably incipiently cuts in each case a plurality of depth structures 12 (for example 4) simultaneously. Mini-statistics about the examined characteristics of the depth structure are thus obtained in each case.

The depth structures characterized according to the different process steps in accordance with the present invention are preferably directly adjacent or lie within a smallest possible region at the surface 14 of the substrate 10. The influence of local variations in the process parameters can be disregarded in this case. The results of the characterization can therefore be attributed solely to the influence of the individual process steps with high accuracy.

One example of a sequence of process steps that can be examined in this way comprises the steps of PHMO (poly hard mask open), DTMO (deep trench mask open), DT (deep trench), wet bottle, HSG (hemispherical grain) deposition.

Figure 6:
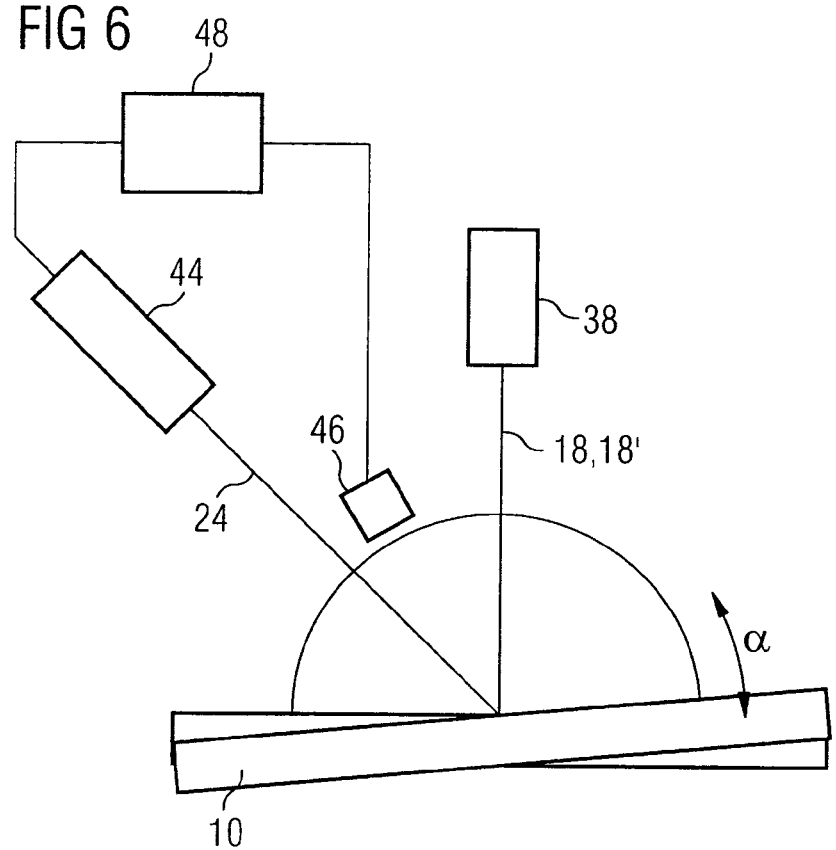
FIG. 6 shows a schematic illustration of an apparatus according to the present invention.

FIG. 6 is a schematic illustration of an apparatus in accordance with the present invention for carrying out the above-described method according to the invention. The apparatus comprises a device 38 for generating the focused ion beams 18, 18', a device 44 for generating the focused electron beam 24, a detector 46 for detecting interaction products that arise when the focused electron beam 24 impinges on the substrate 10, and a control and evaluation device 48. The device 44 for generating the focused electron beam 24, the detector 46 and the control and evaluation unit 48 form for example the essential constituents of a scanning electron microscope. The device 38 for generating the focused ion beams 18, 18' and the device 44 for generating the focused electron beam 24 are preferably arranged in such a way that the ion beams 18, 18' and the electron beam 24 form an angle of approximately 45°.

The substrate 10 is arranged such that it can be tilted or pivoted in the apparatus. During the production of the cutout 20, the substrate 10 is preferably arranged in such a way that the focused ion beam 18 impinges on the substrate 10 perpendicularly to the surface 14. In order to uncover the cut areas 22' (FIGS. 4, 5), the substrate 10 is tilted by the angle α toward the device 44 for generating the focused electron beam 24 in order, as described above with reference to FIG. 3, to remove the layers from the substrate 10 which form the angle α with the normal to the area of the surface 14 of the substrate 10.

The detector 46 is for example a simple counter for electrons from the electron beam 24 that are backscattered from the substrate 10 or secondary electrons generated by electrons from the electron beam 24 in the substrate 10. As an alternative, the detector is energy dispersive in order to analyze the element composition of the substrate 10 near the surface in spatially resolved fashion by means of Auger electron spectroscopy (AES).

As an alternative, the detector 46 is an energy dispersive detector for X-ray photons in order to analyze the element composition of the substrate 10 in spatially resolved fashion by means of energy dispersive X-ray spectroscopy (EDX), the analyzed layer being significantly thicker than in the case of AES.

As an alternative, a wavelength dispersive element (for example an analyzer single crystal) and a (non-energy dispersive) detector for X-ray photons are provided in order to analyze the element composition of the substrate 10 in spatially resolved fashion by means of wavelength dispersive X-ray spectrometry (WDX).

With the use of a focused electron beam 24, both AES and EDX and WDX offer an analysis of the element composition with a spatial resolution down to a few nm.

As an alternative, instead of a focused electron beam, use is made of monochromatic X-ray radiation that generates photoelectrons in the substrate 10. The photoelectrons generated are imaged by means of an electron optical arrangement onto an input of an analyzer for analyzing the kinetic energy of the photoelectrons. A detector detects the photoelectrons in order to analyze the element composition of the substrate 10 in a layer near the surface by means of X-ray photoelectron spectroscopy (XPS).

Figure 7:
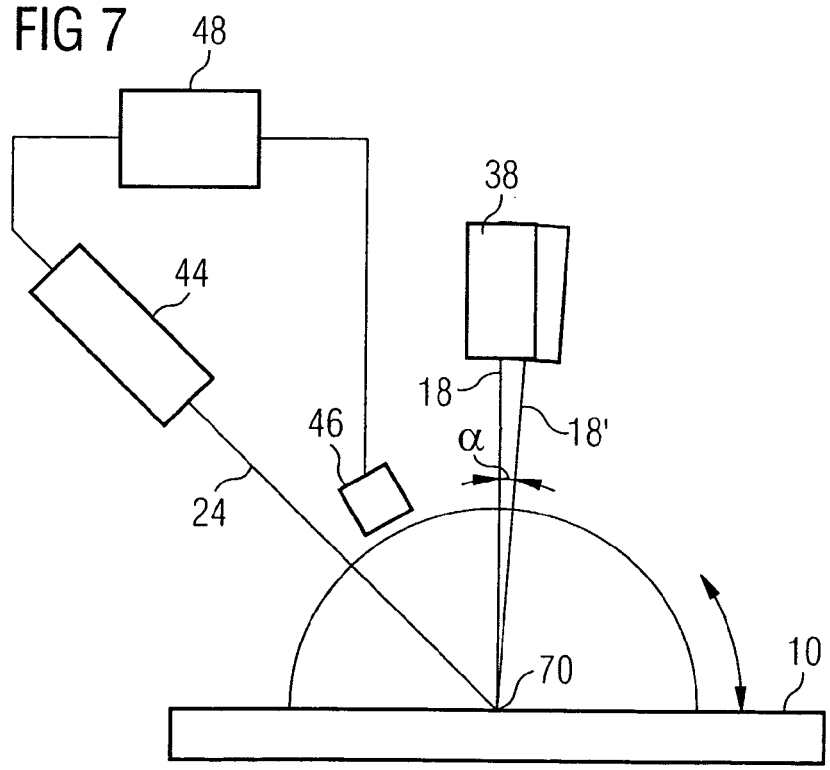
FIG. 7 shows a schematic illustration of an apparatus according to the present invention.

FIG. 7 is a schematic illustration of an apparatus in accordance with a further exemplary embodiment of the present invention. Here, for the purpose of generating the focused ion beam 18' by means of which the cut areas 22' are uncovered, the substrate 10 is not tilted, rather the device 38 for generating the focused ion bean 18' is pivoted by the angle α about the interaction point 70.

As an alternative to the exemplary embodiments illustrated above with reference to FIGS. 3, 4A, 4B, the cut areas 22' are not planar. However, it is in any event advantageous and preferred for the direction of the focused ion beam 18' to run parallel to the cut area 22'.

The present invention, as illustrated above, can be implemented both as a method and as an apparatus. What is more, it can be implemented as a computer program with program code for carrying out the method according to the invention if the computer program is executed on a computer.

LIST OF REFERENCE SYMBOLS

10 Substrate
12 Depth structure
14 Surface of the substrate 10
16 Protection cap
18, 18° Focused ion beam
20 Cutout
22, 22° Cut area
24 Electron beam
26 Arrow
28 Surface
38 Device for generating the focused ion beam 18
44 Device for generating the electron beam 24
46 Detector for detecting interaction products
48 Control and evaluation device
50 Thin wall
52 Cut plane
60 Cross-sectional area of the depth structure 12
62 Zone

What is claimed is:

1. A method for the characterization of a depth structure in a substrate at a surface of the substrate comprising:
producing a cutout at the surface of the substrate between an imaging device and the depth structure, the cutout being spaced apart from the depth structure;
removing a layer of the substrate, which incipiently cuts the depth structure and the cutout, by means of an ion beam to obtain a cut area, the layer and the normal to the area of the surface of the substrate assuming an acute angle that is greater than zero; and
imaging of the cut area by means of the imaging device to characterize the depth structure.

2. The method as claimed in claim 1, in which the cutout is produced by means of an ion beam.

3. The method as claimed in claim 1, in which the ion beam has a direction parallel to the layer.

4. The method as claimed in claim 1, in which the cut area is imaged by scanning electron microscopy or scanning force microscopy and/or is analyzed by means of Auger electron spectroscopy, energy dispersive X-ray spectroscopy, wavelength dispersive X-ray spectroscopy or X-ray photoelectron spectroscopy.

5. The method as claimed in claim 1, in which the producing, removing and imaging are executed multiple times to characterize the depth structure on the basis of images of a plurality of cut areas.

6. The method as claimed in claim 1, wherein in the removing, the depth structure is lengthened in a direction parallel to the direction of the ion beam, and in which a width of the depth structure measured perpendicular to the direction of the ion beam is determined for the characterization.

7. An apparatus for the characterization of a depth structure in a substrate at a surface of the substrate, comprising:
a device for removing a layer of the substrate, which incipiently cuts the depth structure and a cutout at the surface of the substrate by means of an ion beam to obtain a cut area; and
a device for imaging the cut area through the cutout to characterize the depth structure, wherein
the removal device is formed such that the layer and the normal to the area of the surface of the substrate assume an acute angle that is greater than zero.

8. The apparatus as claimed in claim 7, in which the removal device and the imaging device are arranged at a vacuum vessel in such a way that the removal and the imaging can be effected without moving the substrate.

9. The apparatus as claimed in claim 7, in which the imaging device is a scanning electron microscope or a scanning force microscope or comprises a device for Auger electron spectroscopy, X-ray photoelectron spectroscopy, energy dispersive X-ray spectroscopy or wavelength dispersive X-ray spectroscopy.

* * * * *